(12) United States Patent
Stephan et al.

(10) Patent No.: US 9,449,400 B2
(45) Date of Patent: Sep. 20, 2016

(54) METHOD FOR CHARACTERISING VOLUMES OF SKIN

(71) Applicant: LVMH RECHERCHE, Saint Jean de Braye (FR)

(72) Inventors: Sandrine Stephan, Beaugency (FR); Rodolphe Korichi, Saint Jean le Blanc (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 14/429,636

(22) PCT Filed: Sep. 25, 2013

(86) PCT No.: PCT/FR2013/052263
§ 371 (c)(1),
(2) Date: Mar. 19, 2015

(87) PCT Pub. No.: WO2014/049271
PCT Pub. Date: Apr. 3, 2014

(65) Prior Publication Data
US 2015/0248773 A1 Sep. 3, 2015

(30) Foreign Application Priority Data

Sep. 26, 2012 (FR) .................................. 12 59046

(51) Int. Cl.
*G06K 9/00* (2006.01)
*G06T 7/40* (2006.01)
(Continued)

(52) U.S. Cl.
CPC .............. *G06T 7/407* (2013.01); *A45D 44/005* (2013.01); *A61B 5/0077* (2013.01); *A61B 5/442* (2013.01); *G01B 11/00* (2013.01); *G06K 9/00275* (2013.01); *G06T 7/0016* (2013.01); *A45D 2044/007* (2013.01); *G06T 2207/10012* (2013.01); *G06T 2207/10028* (2013.01);
(Continued)

(58) Field of Classification Search
CPC ............................................. G06T 2207/30088
See application file for complete search history.

(56) References Cited

U.S. PATENT DOCUMENTS 8,218,862 B2 * 7/2012 Demirli .................. A61B 5/441
382/162
8,238,623 B2 * 8/2012 Stephan ................. A61B 5/442
382/100

(Continued)

FOREIGN PATENT DOCUMENTS

EP          1298562      4/2003
JP         2008-093048    4/2008

(Continued)

OTHER PUBLICATIONS

Ahn et al. (KR 10-2007-0032493) English translation.*

(Continued)

*Primary Examiner* — Soo Park
(74) *Attorney, Agent, or Firm* — Hamre, Schumann, Mueller & Larson, P.C.

(57) ABSTRACT

The subject of the present invention is a method for characterizing the distribution of the volumes of the surface of the skin of an individual, more particularly applicable in the evaluation of the effect of firming cosmetic products. This method uses the isolines and the gradients of the slopes computed from a three-dimensional representation of the surface of the skin.

13 Claims, 2 Drawing Sheets

Figure 1:
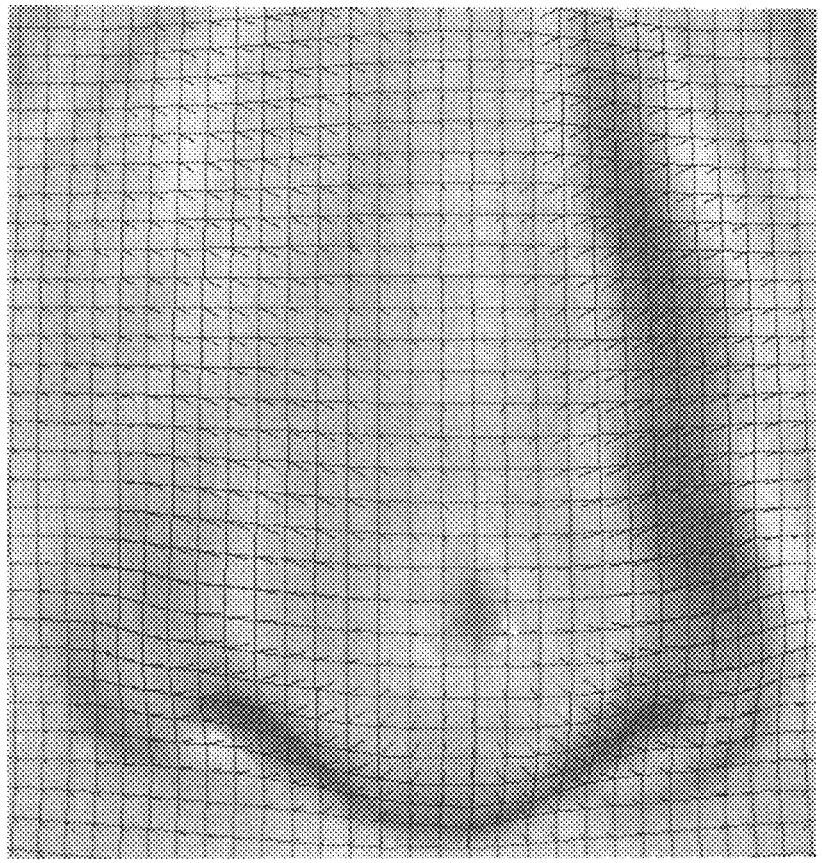

(51) Int. Cl.
　　*A61B 5/00*　　　(2006.01)
　　*G06T 7/00*　　　(2006.01)
　　*A45D 44/00*　　(2006.01)
　　*G01B 11/00*　　(2006.01)

(52) U.S. Cl.
　　CPC ............. *G06T2207/20036* (2013.01); *G06T 2207/30088* (2013.01); *G06T 2207/30201* (2013.01)

(56) References Cited

U.S. PATENT DOCUMENTS

| | | | | |
|---|---|---|---|---|
| 8,391,639 | B2* | 3/2013 | Hillebrand | G06T 7/0028 345/639 |
| 8,861,863 | B2* | 10/2014 | Chhibber | G06F 19/321 382/190 |
| 8,988,686 | B2* | 3/2015 | Hillebrand | A45D 44/005 356/421 |
| 9,384,543 | B2* | 7/2016 | Stephan | G06T 7/0012 |
| 2005/0257748 | A1* | 11/2005 | Kriesel | A01K 11/008 119/51.02 |
| 2008/0194928 | A1* | 8/2008 | Bandic | A61B 5/411 600/306 |
| 2011/0040192 | A1* | 2/2011 | Brenner | A61B 5/0059 600/476 |
| 2013/0050434 | A1* | 2/2013 | Kim | G06T 17/00 348/47 |

FOREIGN PATENT DOCUMENTS

| | | |
|---|---|---|
| KR | 2007-0032493 | 3/2007 |
| WO | 2012/001289 | 1/2012 |

OTHER PUBLICATIONS

Park et al. (KR 10-2012-0020960) English translation.*
Takasaki, "Moire tomography", Applied Optics, vol. 9, No. 6, Jun. 1970.*
Saito et al. "Development of a new evaluation method for cheek sagging using a moire 3D analysis system", Skin Research and Technology 2008; 14; 287-292.*
International search report for International application No. PCT/FR2013/052263, dated Aug. 1, 2014 (3 pages).

* cited by examiner

METHOD FOR CHARACTERISING VOLUMES OF SKIN

The subject of the present invention is a method for characterizing the distribution of the volumes of the surface of the skin of an individual, more particularly applicable in evaluating the effect of firming, restructuring and tensor cosmetic products.

The visual perception of the face of a person and the age that can be associated therewith depends largely on the quality of the distribution of the volumes of the skin of the face. Also, the perception of the youthfulness of a face is greatly affected by the modification of its volumes which can be provoked by the appearance of wrinkles or by the relaxation of the skin as a result of ageing.

The inventors have developed a novel instrumental characterization method that makes it possible to map at least a part of the bodily surface of an individual (body and/or face), and to measure its morphological variations. This method makes it possible to compare the trend of the distribution of the volumes of the bodily surface in one and the same individual over time, or to compare the distribution of these volumes from one individual to another.

PRIOR ART

The literature abundantly demonstrates the benefit of the Moiré technique (optical triangulation by phase shifting) for mapping surfaces and plotting curvatures on numerous media with a few applications when it comes to the face. The Moiré technique consists in projecting onto a surface the shadow of the periodic distribution of geometrical shapes such as fringes, points or a grid. The lines are produced by the projection of the shadow of the geometrical shapes generated by a light source on the surface whose relief is to be studied.

There are also various methods that make it possible to determine three-dimensional shapes of a surface, and notably that of a face. The most widely used is that of the Moiré technique associated with fringe projection.

Finally, it has recently been proposed to measure the elasticity of the skin by using a Moiré image in the application KR 2007-32493. The method consists in photographing two Moiré images, and the index of elasticity can be defined in two different ways. According to a first variant, the Moiré image corresponds to the shadow of two circles projected onto the surface of the left cheek of the face. On this first photograph, the maximum deviation and the minimum deviation between the two circles are measured, and the index of elasticity corresponds to the ratio between the minimum deviation and the maximum deviation between the two curvatures. According to a second variant, the image is the projection of a horizontal line starting from the commissure of the lips of the left side of the face. The angle that the projected curvature forms with the line tangential to the contour of the lips passing through the commissure of the lips is measured, and the index of elasticity corresponds in this case to the value of this angle.

While these methods make it possible to accurately quantify the morphological variations like the oval of a face or even the relaxation of the volumes over time, the fringe projection apparatus is bulky and non-portable apparatus requiring a repositioning table to install the subject and two cameras.

Furthermore, the facial plotting of the level curvatures in two dimensions by this method does not make it possible to achieve a satisfactory level of resolution. None of these methods is accurate enough to visualize and quantify the morphological variations of a face in three dimensions, more particularly in demonstrating cosmetic effects.

The method described in the application EP 1 298 562 relies on the superposition of two 3D images in order notably to measure the thinning of the oval of the face or the increase in the surface area of the eyes following the application of a tensor product. The method of the invention, by contrast, comprises the computation of a parameter characterizing the very surface of the face, and makes it possible to dispense with the difficulties related to the superposition of two images taken at two different moments. The method of the invention also makes it possible to make comparisons against a reference panel, whereas the prior art method makes it possible only to measure the trend of the state of the skin for one and the same individual.

DESCRIPTION OF THE INVENTION

The present invention provides a method for characterizing the distribution or the migration of the volumes on the surface of the body of an individual, which volumes are characterized and quantified accurately, reproducibly and significantly, by computing and by comparing certain parameters characteristic of the relief of said surface. This contactless in-vivo method makes it possible advantageously to propose parameters which are correlated significantly with the visual perception that an expert or a user can have of the surface of the skin.

According to one of its aspects, the subject of the invention is therefore a method for characterizing the distribution or the migration of the volumes on the surface of the skin of an individual, said method comprising the following steps:

i) determining a reference value from the individual or from at least one other person, by
   acquiring a three-dimensional image in voxel form, representative of the surface of at least a part of the body of said individual or of said person,
   selecting at least one line of said image in the form of a three-dimensional surface, possibly matched with the graphic representation of this line,
   computing at least one parameter correlated with said line, to obtain a first value, called reference value, ii) determining a second value of said parameter by applying the step i) to the individual, preferably at a different time, iii) a step of estimating the distribution or the migration of the volumes on the surface of the skin of the individual which consists in comparing the second value to the reference value.

Imaging

To study the surface of the body, it is preferable to produce a three-dimensional (3D) image which can be obtained by a number of methods known to those skilled in the art. In the context of the present invention, it is preferable to produce a three-dimensional image of the bodily surface by a so-called "passive vision" based input, preferably by passive stereoscopy.

Stereoscopy offers the advantage of mimicking human vision, therefore making it possible to visualize the surface of the body in 3D and reconstruct its surface in 3D. The principle of passive stereoscopy consists in reconstructing, via standardized photographed area capture angle and distance conditions, a three-dimensional scene from two two-dimensional images of the observed scene.

The hardware used is generally a camera provided with a self-calibration or absolute calibration system. Self-calibration makes it possible to plot the surface with fewer data than the absolute calibration system.

The images are preferably produced using a camera capable of simultaneously taking two images in two dimensions in a single shot, and of constructing an image in three dimensions using a computer reconstruction algorithm. The image is advantageously in voxel form.

The surface of the body of the individual can be photographed regardless of the position of the body of the individual, for example when the individual is seated, standing or lying down.

When the variation of the volumes of the face of an individual are to be studied, it is preferable to take the photograph of the individual in the seated position from the front.

Advantageously, an area of interest of the image which has been acquired is delimited, and the computation is performed on said area of interest.

For example, an image of all of the face of the individual is acquired and the area of interest can then be a cheek, an eyelid or even the oval of the face. The area of interest of the image acquired can be delimited by applying a reference model, that can be transposed from one individual to another or for one and the same individual from one shot to another.

The reference model of the area of interest has, for example, a given surface value, and it is, for example, delimited by at least one anatomical landmark chosen from the nasolabial fold, the position of the eyes, the tip of the nose, the point of the chin and the corners of the mouth.

The area of interest is preferably square or essentially circular, centered on the left or right cheekbone of the individual, and delimited by the nasolabial fold.

Advantageously, a reference model of the anatomical regions of interest can be defined, and in such a way as to propagate said model, semi-automatically, to the individual to which the method of the invention is applied.

The reference model can consist of an image of a reference subject on which the user of the method can identify a certain number of anatomical landmarks, for example the position of the eyes, of the tip of the nose, of the corners of the mouth and of the chin.

The mapping of the duly defined model with the image of the individual can be done by means of the definition of these same points in said image. The area of interest can be defined on the reference subject by means of spline curvatures which become available on the individual.

Determination, Display and Analysis of the Lines

To give an idea of the relief, the surface is preferably represented by a set of level lines (or level curvatures, or even isolines), each of said level lines consisting of all the points of the same altitude relative to a reference plane that the user of the method of the invention can define manually. Preferably, the plane perpendicular to the exposure axis passing through the tip of the nose of the individual is chosen as reference plane.

The shape and the orientation of these isolines make it possible to characterize the morphology but also the variations of the surface such as, for example, those due to the migrations of the volumes. Volume migrations are often the result of the relaxation of the skin due to ageing: a reduction of the firmness of the skin makes it more dependent on its own weight, and a ptosis of the skin of the face is thus for example frequently observed.

The direction of the isolines and their curvatures also make it possible to visualize the morphological deformation of the surface of the skin, and notably of a face. For example, between an elderly and youthful face, differences are observed in the values of the curvatures and the form of the curvatures. The isolines of an elderly face are more "closed" than the isolines of a youthful face which are more regular and more "open".

According to one embodiment of the invention, at least three lines representing the surface are selected from the image, namely at least one isoline, one peak line and one trough line. A set of isolines is for example selected, for which the altitudes are spaced apart by 0.1 to 2 mm, preferably by approximately 1 mm.

The parameter advantageously corresponds to the number of corner points of said at least one isoline, the corner points corresponding to the points of intersection of the isoline with the peak line and the trough line. The corner points correspond to extremes of the curvature (minimum or maximum) along the isoline.

The parameter can also correspond to the maximum or the minimum of the curvatures which are measured at the corner points of the isoline. A smoothing parameter as well as a curvature threshold parameter can be introduced into the computation of the corner points in order to avoid detecting very small undulations.

The parameter can also correspond to the amplitude of the extreme curvatures of the isoline. This parameter makes it possible to quantify the amplitude of the curvature of the isoline when it is situated on a lump (maximum or crest curvature) or in a trough (min curvature).

Determination of the Directions of the Volumes

According to another embodiment of the invention, the surface of the body of the individual can be represented by the lines of a polyhedral meshing belonging to the image.

It is notably possible to compute the gradients of each of the vertices of this polyhedral meshing, and the parameter can, for example, be the mean of the directions of the gradients of the vertices of the polyhedral meshing, or the width of the distribution of the directions of the gradients of the vertices of the polyhedral meshing.

The measurement of the main directions of the volumes illustrated by the isolines can be performed by computing the gradient vector for each voxel of the image or for each vertex of the polyhedral meshing. The gradient vector has a component x (projected from the vector onto the horizontal axis) and a component y (projected from the vector onto the vertical axis corresponding to the exposure axis). If the variation of the directions of the volume is significant, the norm of the vector is significant. If the change of direction is greater relative to the horizontal axis, the x component becomes more significant than the y component. Finally, if the variation of direction of the volume is more significant relative to the vertical axis, the y component becomes more significant than the x component.

The direction of the gradients can be measured from the captured image and relative to a reference axis, such as, for example, an angle of 45°.

The angle $\theta$ (angle of the gradient vector relative to the horizontal, also called direction of the gradient) is notably representative of the predominance of one of the components (x or y): if $\theta=45°$ then x=y, if $\theta>45$ then y>x and if $\theta<45$ then x>y.

The higher the algebraic value of the mean angle of the gradients, the greater the ptosis of the skin.

The distribution of the directions of the gradient corresponds to the spread of the histogram of the directions of the gradient. The greater the number of different gradient directions on an area, the greater the spread of the histogram and the more irregular the surface of the area studied.

All the parameters which have just been described can be computed according to the formulae given in the thesis entitled "Mise en correspondance automatique d'images médicales tri-dimensionnelles" (Automatic mapping of three-dimensional medical images), Jean-Philippe Thirion, Accreditation to supervise research, 5 Jun. 1997, University of Nice, Sophia-Antipolis.

The reference value of the parameter can be determined from the value of the parameter computed on at least two different people belonging to a reference group. The reference group can be, for example, defined as being an age category of individuals of the same sex. The reference value can be the mean of the at least two values obtained in the reference group.

A reference group will preferably be chosen in which the sex and the age category correspond to that of the individual. It will also be possible to choose a reference group in which the people have anatomical landmarks in a configuration close to that of the individual.

The method of the invention can comprise the determination of at least two parameter values. The first measurement and the second measurement take place at a different time inasmuch as, between these two measurements, a more or less lengthy time period elapses during which the state of the individual is modified relative to a so-called "reference" state for the implementation of the method of the invention. Thus, this time period can be a few minutes but can range up to several years, depending on the state selected.

Thus, according to one alternative of the method of the invention, the reference value of the parameter is computed according to the method for a first state of the individual, and the parameter is then computed for at least one other state of the same individual. The state of the individual can be his or her age or the position of his or her body upon the acquisition of the image.

The reference state can be prior to the application of a cosmetic treatment and the acquisition of the image can follow the application of a cosmetic treatment.

The method of the invention can, in this alternative, be implemented to evaluate the ptosis of the face of an individual due to the ageing over time.

According to one of its aspects, another subject of the invention is a method for selecting a cosmetic agent or a cosmetic composition likely to improve the state of firmness and of tension of the skin, to counter the relaxation of the skin, or to counter the loss of elasticity of the skin, said selection method comprising the implementation of the characterization method described previously.

The invention relates also to a method for evaluating the effectiveness of a cosmetic agent or of a cosmetic composition, in particular to improve the state of firmness and of tension of the skin, to counter the relaxation of the skin, or to counter the loss of elasticity of the skin of at least one individual having need thereof, characterized in that the characterization method described previously is implemented by applying said cosmetic agent or said composition to the skin of the individual between the steps i) and ii), and
 by concluding on the effectiveness or the lack of effectiveness of said cosmetic agent after the comparison step iii).

The cosmetic product can notably be a tensor, firming or anti-ageing product. Said method for evaluating the effectiveness can be implemented to evaluate the effects of the application of a tensor, firming or anti-ageing cosmetic product on the modification of the distribution of the volumes of the face of an individual, in particular on the shape of the oval of the face.

According to yet another of its aspects, a subject of the invention is a method for evaluating the trend of the level of firmness or of relaxation of the skin in one and the same individual, said evaluation method comprising the implementation of the characterization method described previously in which the reference value is determined for a first state of the individual.

The invention is described in more detail with reference to the following figures and examples.

FIG. 1 reproduces a meshing of square vertex representing the surface of the face of an individual.

Figure 2:
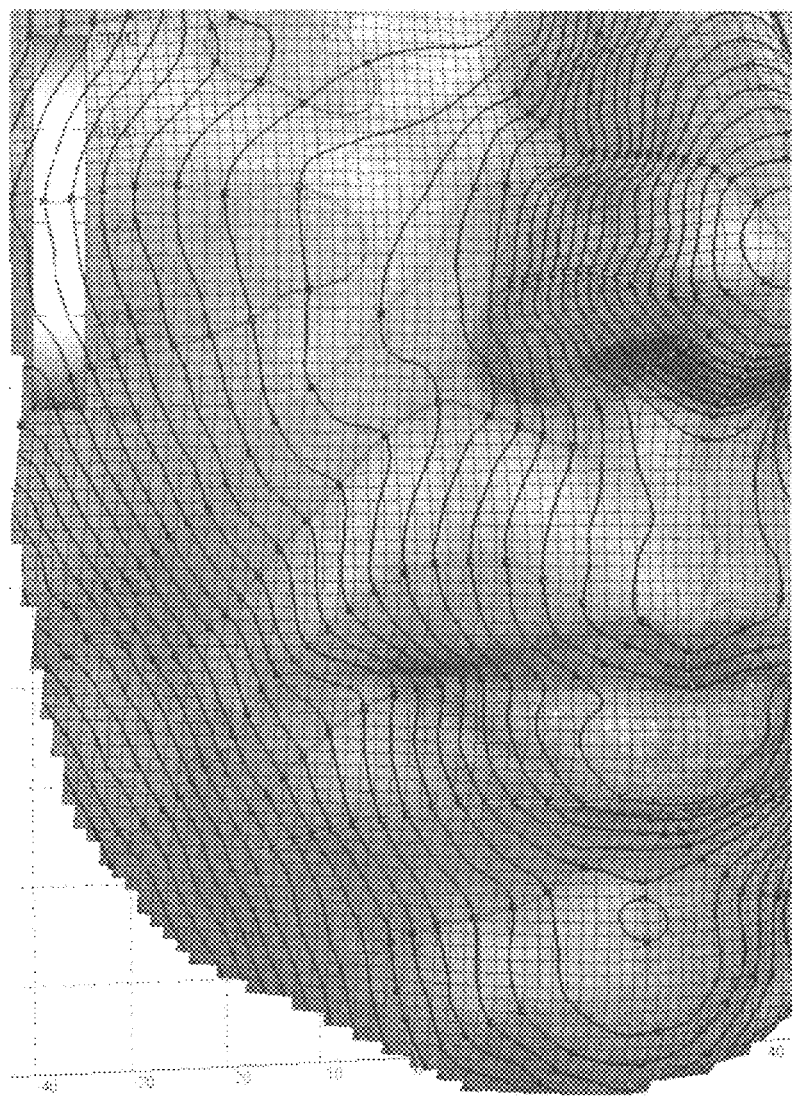

FIG. 2 represents the isolines, the peak lines and the corner points of the surface of the face of an individual.

The faces of 40 women aged from 21 to 86 years not having undergone any cosmetic surgical operation were photographed in standardized light, distance and angle conditions.

For the exposure in passive stereoscopy, two identical camera apparatuses are used with optical viewfinding equipped with an 18 million pixel (5184×3456 pixel) CMOS sensor and a lens of 60 mm fixed focal length. The two apparatuses are positioned at the same distance from the individual being photographed, and at 30° on either side of the median axis at right angles to the plane of the area to be photographed.

The area of interest is a 5 cm by 4 cm rectangle positioned diagonally on the cheek.

The photo is taken with the mouth closed, hair tied back to clear the face. The exposure is triggered simultaneously for the two apparatuses so as to obtain two photographs at an angle of 60° from one another.

Two groups were formed: a first group of 20 women (average age=32 years+/−10 years) and a second group of 20 women (average age=59 years+/−20 years).

The apparatus was provided with an absolute calibration system and set up for a field of view of 20×20 cm.

Parameters of the apparatus for the exposure:
 $1/200$—shutter speed.
 F00—aperture.
 M—indicates manual setting mode.
 Flash exposure depending on ambient light.
 Iso 100—camera light sensitivity mode.
 "Flash" white balance.
 Partial metering mode.
 One shot.
 L—indicates image storage quality.
 Central manual auto focus point selected.

The exposure axis and distance are defined by marking the base of the nostrils of each woman with two light rays emitted by the apparatus. Once the two rays have merged, the apparatus is moved so that the two rays reach the tip of the nose and the photo is taken.

A three-dimensional image has been reconstructed in a conventional manner from the two images taken by the apparatus. This image can be viewed with the Cortona VRML software. An area of interest has been chosen that is on the right or left cheek of the two-dimensional images close to the nasolabial fold of the first woman of the group. This area is a 5 cm by 4 cm rectangle, positioned diagonally on the cheek as indicated in the study document. This area of interest was then propagated to all the other images.

The isolines 1 mm apart were computed relative to the plane passing through the tip of the nose and at right angles to the exposure axis.

A square vertex meshing of side equal to 1 mm was also computed and represented (see FIG. 1).

The direction of the curvatures was computed from the gradient vectors on the vertex meshing and a reference direction specified by the user. The value was expressed in degrees ranging from −180 to +180.

The values of the curvatures were computed from the angle between the surface gradient and the horizontal plane (plane corresponding to the face plane). The value was expressed in degrees ranging from 0 to 90, 0 corresponding to a zero curvature and 90 to a vertical surface.

Each computation was performed by using the result sigma=2 to avoid introducing too much smoothing on the original meshing and to deactivate the "fix planarity" option. All the angles are expressed in degrees.

On the right part of the face, the mean direction of the curvatures is equal to −21.9° which means that this mean direction is slightly less than the 45° reference direction. On the left part, the symmetrical value is equal to 24.1° relative to the 135° reference direction.

The results between the right and left parts are fairly different because the axis Z does not correspond exactly to the axis of the face. Consequently, the gradient values and the isolines are not symmetrical.

The function of the isoline curvature was also examined on the 3D surface. The derivative of this function y is also available and is used in order to determine the extremes of the curvature function. In effect, the positions in which the function has a zero value define the curvatures which correspond to the incurvation of the curvatures at the ends, at the peaks and in the troughs of the surface.

The number of corner points corresponds to the number of intersections between the isolines and the incurvation of the curvatures at the ends. "Trough curvature" and "Crest curvature" correspond to the incurvation value at the ends on these points. For this computation, the isoline spacing was 1 mm with a value sigma=3 (see FIG. 2).

TABLE 1

|  | Young face (n = 20, average 32 years) | Elderly face (n = 20, average 59 years) | Significance level |
|---|---|---|---|
| Mean direction of the gradient (relative to the 45° reference angle, right cheek) | −26.2° | −17.6° | S (p = 0.02) |
| Mean variation of the gradient (relative to the 45° reference angle, right cheek) | 21.1° | 29.5° | S (p < 0.01) |
| Mean "Crest curvature" | 0.17 | 0.35 | S (p = 0.02) |
| Mean "Trough curvature" | 0.16 | 0.24 | S (p = 0.03) |
| Number of corner points | 36 | 34.7 | S (p < 0.03) |

Overall, the results show that the study of the gradients and of the curvatures makes it possible to distinguish the group of young women and the group of elderly women. These parameters are therefore clearly representative of the physiological phenomena of ageing, more particularly of the ptosis of a face.

The method of the invention allows for objective measurements of cutaneous ageing.

The cheeks of the elderly people give the impression of sagging which is reflected here in a lower maximum slope direction. It is also observed that the more relaxed the skin becomes, the more the directions of the maximum curvature are spread. The curvature of the isolines increases also with age.

The invention claimed is:

1. A method for characterizing the distribution or the migration of volumes on the surface of the skin of an individual, said method comprising the following steps:
   i) determining a reference value from the individual or from at least one other person, by
      acquiring a three-dimensional image in voxel form by passive stereoscopy that represents a three-dimensional surface of at least one part of the body of said individual or of said person,
      selecting at least one line of said three-dimensional surface, and making a graphic representation of said line, wherein lines of a polyhedral meshing of the image are selected, and
      computing at least one parameter correlated with said lines, and obtaining a first value, called a reference value,
   ii) determining a second value of said parameter by applying step i) to the individual, and
   iii) estimating the distribution or the migration of the volumes on the surface of the skin of the individual, by comparing the second value to the reference value, wherein the at least one parameter is a mean of directions of the gradients of vertices of the polyhedral meshing.

2. The characterization method as claimed in claim 1, wherein at least three lines are selected: namely an isoline, a peak line and a trough line.

3. The characterization method as claimed in claim 1, wherein one of said at least one parameter further comprises the number of corner points of the isoline.

4. The characterization method as claimed in claim 1, wherein one of said at least one parameter corresponds to the maximum or to the minimum of the curvatures which are measured at corner points of the isoline.

5. The characterization method as claimed in claim 1, wherein the at least one parameter further comprises a width of distribution of directions of the gradients of vertices of the polyhedral meshing.

6. The characterization method as claimed in claim 1, wherein an area of interest is delimited from the image which has been acquired, and in that the computation is performed on said area of interest.

7. The characterization method as claimed in claim 1, wherein the step i) is implemented on at least two different persons belonging to the same age category, and that the reference value is the mean of the at least two values obtained.

8. A method for selecting a cosmetic agent or a cosmetic composition likely i) to improve the state of firmness of the skin, ii) to counter the relaxation of the skin, or iii) to counter the loss of elasticity of the skin, said selection method comprising the implementation of the characterization method as claimed in claim 1.

9. A method for evaluating a cosmetic agent or a cosmetic composition regarding its effectiveness i) to improve the state of firmness of the skin, ii) to counter the relaxation of the skin, or iii) to counter the loss of elasticity of the skin of at least one individual in need thereof, characterized in that the characterization method as claimed in claim 1 is implemented:
   by applying said cosmetic agent or said composition to the skin of the individual between steps i) and ii), and by concluding on the effectiveness or the lack of effectiveness of said cosmetic agent or said composition after the comparison step iii).

10. A method for evaluating the trend of the firmness level or of the relaxation level of the skin in one and the same individual, said evaluation method comprising the implementation of the characterization method as claimed in claim 1 in which the reference value is determined for a first state of the individual.

11. The method of claim 1, wherein said passive stereoscopy comprises reconstructing the three-dimensional image from two two-dimensional images of the at least one part of the body of said individual or of said person.

12. A method for characterizing the distribution or the migration of volumes on the surface of the skin of an individual, said method comprising the following steps:
   i) determining a reference value from the individual or from at least one other person, by
      acquiring a three-dimensional image in voxel form by passive stereoscopy that represents a three-dimensional surface of at least one part of the body of said individual or of said person, wherein said passive stereoscopy comprises reconstructing the three-dimensional image from two two-dimensional images of the at least one part of the body of said individual or of said person, said two two-dimensional images being produced using one or two camera(s) simultaneously taking two images in two dimensions in a single shot, and of constructing said image in voxel form in three dimensions using a computer reconstruction algorithm,
      selecting at least one line of said three-dimensional surface, and making a graphic representation of said line, wherein lines of a polyhedral meshing of the image are selected, and
      computing at least one parameter correlated with said line, and obtaining a first value, called a reference value,
   ii) determining a second value of said parameter by applying step i) to the individual, and
   iii) estimating the distribution or the migration of the volumes on the surface of the skin of the individual by comparing the second value to the reference value,
   wherein the at least one parameter is a mean of directions of gradients of vertices of the polyhedral meshing.

13. The method of claim 12, wherein two cameras are positioned at the same distance from the individual or person being photographed, and at 30° on either side of a median axis at right angles to a plane of the at least one part of the body of said individual or of said person.

* * * * *